United States Patent [19]

Lee, Jr.

[11] Patent Number: 4,989,616
[45] Date of Patent: * Feb. 5, 1991

[54] MONOSTATIC ANTI-BRUXISM DEVICE

[76] Inventor: Alexander Y. Lee, Jr., 1075 S. Jefferson St., Apt. 321, Arlington, Va. 22204

[*] Notice: The portion of the term of this patent subsequent to Jun. 13, 2006 has been disclaimed.

[21] Appl. No.: 399,017

[22] Filed: Aug. 28, 1989

[51] Int. Cl.$^5$ ............................................. A61B 5/103
[52] U.S. Cl. ................................. 128/777; 128/905; 128/859; 73/582; 340/573
[58] Field of Search ............... 128/773, 774, 777, 859, 128/861, 660.01, 660.02, 660.06, 905; 73/589, 597, 598; 340/573, 575

[56] References Cited

U.S. PATENT DOCUMENTS

Re. 32,782 11/1988 Pratt, Jr. .......................... 128/660.06
4,570,486 2/1986 Volkmann ............................. 73/597
4,838,283 6/1989 Lee .......................................... 128/777

Primary Examiner—Max Hindenburg
Assistant Examiner—Robin R. Longo
Attorney, Agent, or Firm—Jerry C. Lyell

[57] ABSTRACT

An apparatus and method for the control and prevention of bruxing (nocturnal teeth grinding) which comprises a sound generating means affixed to the jaw of the user, an electronic control means to "read" electrical impedance variations within said sound generating means caused by bruxing and to activate an alarm when bruxing occurs. Said apparatus utilizes the principle of bone conduction wherein sonic loading of said sound generating means differs between the open-jaw and the closed-jaw states. The alarm develops a conditioned reflex in the user such that after the first few alarms incident to bruxing the user does not awaken but merely reacts by relaxing the jaw when the alarm occurs.

2 Claims, 2 Drawing Sheets

MONOSTATIC ANTI-BRUXISM DEVICE

BACKGROUND OF THE INVENTION

Bruxism is the condition of nocturnal teeth grinding which afflicts many people and which is widely considered to be a psychological stress reaction. The condition produces abnormal wear of the molar teeth of the afflicted person and is a source of annoyance and disturbance to anyone who sleeps in the near vicinity of such a person.

Several devices have been patented which were designed to relieve the condition of bruxism. Among such devices are the Samelson inventions, U.S. Pat. Nos. 4,169,473 and 4,304,227. These inventions consist of molded devices designed to be inserted into the mouth of a person who experiences snoring and bruxism during sleep. The object of these inventions is to prevent nocturnal teeth grinding by means of an intervening physical barrier and to prevent snoring by means of forced nasal breathing.

Another device, the Ober invention, U.S. Pat. No. 4,669,477 is an electronic instrument which operates by detecting electromyographic signal voltages from the mandibular musculature during bruxing. The device then imparts an electrical stimulation to the jaw of the bruxing person, which stimulation is intended to cause the jaw muscles to relax and allow the jaw to open. The Ober disclosure does not, however, reveal how said stimulation will selectively stimulate the particular muscle fibers that cause the jaw to open rather than resulting in the tonus of all the muscle fibers in the region of the stimulation.

These devices have obvious shortcomings in both design and effect, some of which are overcome by the relative simplicity of the present invention which uses the principle of bone conduction to activate an alarm signal which then develops a conditioned reflex to interrupt the bruxing pattern with a minimum of mental or physical intrusion.

SUMMARY OF THE INVENTION

The present invention is a novel apparatus and method for the control and prevention of bruxism (nocturnal teeth grinding). The apparatus comprises a single sound generating means (monostatic means) which can be affixed (for example, with adhesive) to appropriate locations on the face of a person who experiences bruxism and jaw clenching while sleeping. The device operates on the principle that sonic vibrations travel much better through relatively rigid bone and dental tissue than through softer tissue such as ligaments. For the purpose of conducting or transmitting sound an open or unclenched mandible is "soft coupled" to the skull by means of ligaments and muscle while a closed or clenched mandible is "hard coupled" to the skull. Thus, if the sound generating means is affixed to the side of the jaw, said sound generating means will be driving an essentially isolated jawbone when the mandible is open. When the mandible is closed, the sound generating means will be driving both the jawbone and the upper part of the skull. Accordingly, sonic loading on the sound generating means will differ between the open-mandible and closed-mandible states. This change in sonic loading will produce a corresponding change in electrical impedance of the sound generating means. This change in electrical impedance can therefore also be used to detect the occurrence of bruxism in a sleeping person.

In operation, the sound generating means is connected to an electronic control system such that sound waves of any desired frequency or amplitude can be transmitted to the jaw of a sleeping person via the sound generator (transducer). Transducer impedance variations due to bruxing are processed through an impedance bridge to produce a resultant amplitude-modulated signal. The resultant signal is amplified, rectified, further amplified and electronically integrated to produce a waveform whose amplitude will activate an audible alarm device when teeth clenching occurs. The electronic control system can produce signals that will result in the sound generated being in either the ultrasonic or subsonic ranges and will therefore be inaudible to the user of the device.

The alarm need not necessarily be an audible one. It could include flashing lights or any other sensory stimulus.

The electronic control system is further designed to detect the characteristic clenching pattern or "clenching frequency" of the person who experiences bruxism so that miscellaneous signals and noise do not activate the alarm system.

The electronic control system in this invention is the same control system that was disclosed in U.S. Pat. No. 4,838,283 which claimed a bistatic anti-bruxism device by this inventor, Alexander Y. Lee, Jr.

The use of an audible alarm to alert the sleeping person when teeth clenching occurs will not result in significant disturbance of the periods of sleep. The decibel level of the alarm means can be set to an intensity just sufficient to awaken the sleeping person on the first few occasions of teeth clenching. The initial experiences of responding to the alarm will result in the development of a conditioned reflex such that after the user has adapted briefly to the device, then the sounding of the alarm will stimulate the user to relax and unclench the teeth without returning to a state of consciousness. The principals of establishing spinal reflex arcs are well understood by experimenters and practitioners of psychology and operant conditioning.

BRIEF DESCRIPTION OF THE DRAWINGS

The invention may be further understood by reference to the drawings in which.

DESCRIPTION OF THE PREFERRED EMBODIMENT

Figure 1:
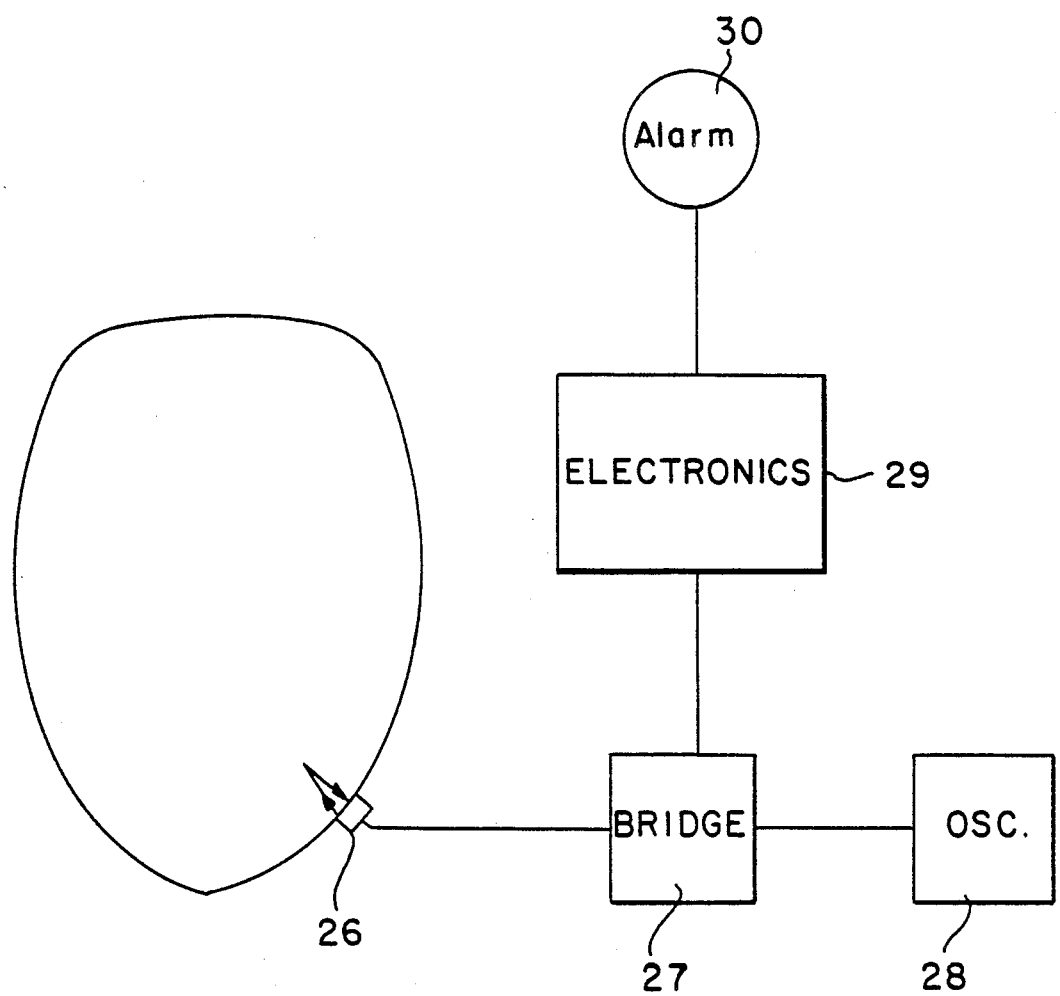
FIG. 1 is a sketch of the elements of the monostatic embodiment of the invention in relation to the user.

Referring now to FIG. 1 of the drawings, a sound generating means 26 is positioned as shown on the jaw of the uses. The impedance to the drive voltage of the sound generating means is a function of sound loading by the bone and tissue. The impedance will characteristically vary for a given drive voltage as the jaw is opened and closed. Said impedance is measured by an impedance comparison means 27 such as an impedance bridge. Said impedance measuring means is located on-line between the signal generator 28 and the sound generator 26.

Impedance bridge 27 incorporates a "dummy" impedance closely approximating the actual sound generator impedance and a means for balancing this "dummy"

impedance against the actual sound generator impedance. The bridge circuit is adjusted for balance with the mandible open, so that the sonic frequency voltage fed to electronics 29 is of minimum amplitude. Closing the mandible produces a change in sound generator impedance which alters the bridge balance and increases amplitude of the sonic frequency voltage fed to electronics 29.

By way of example, if the teeth are opened and closed on the average of once each second, amplitude of the sonic frequency voltage fed to electronics 29 will go from low to high once each second. Hence, the signal fed to electronics 29 will be a sonic frequency voltage carrying squarewave amplitude modulation at the 1 Hz "clenching frequency."

It is the object of electronics 29 to discriminate between the signal conditions when no bruxing is occurring and the signal conditions when bruxing is present and thence to activate alarm 30. A further object of the electronics is to discriminate against transients and stray signals which might false-alarm the device.

Figure 2:
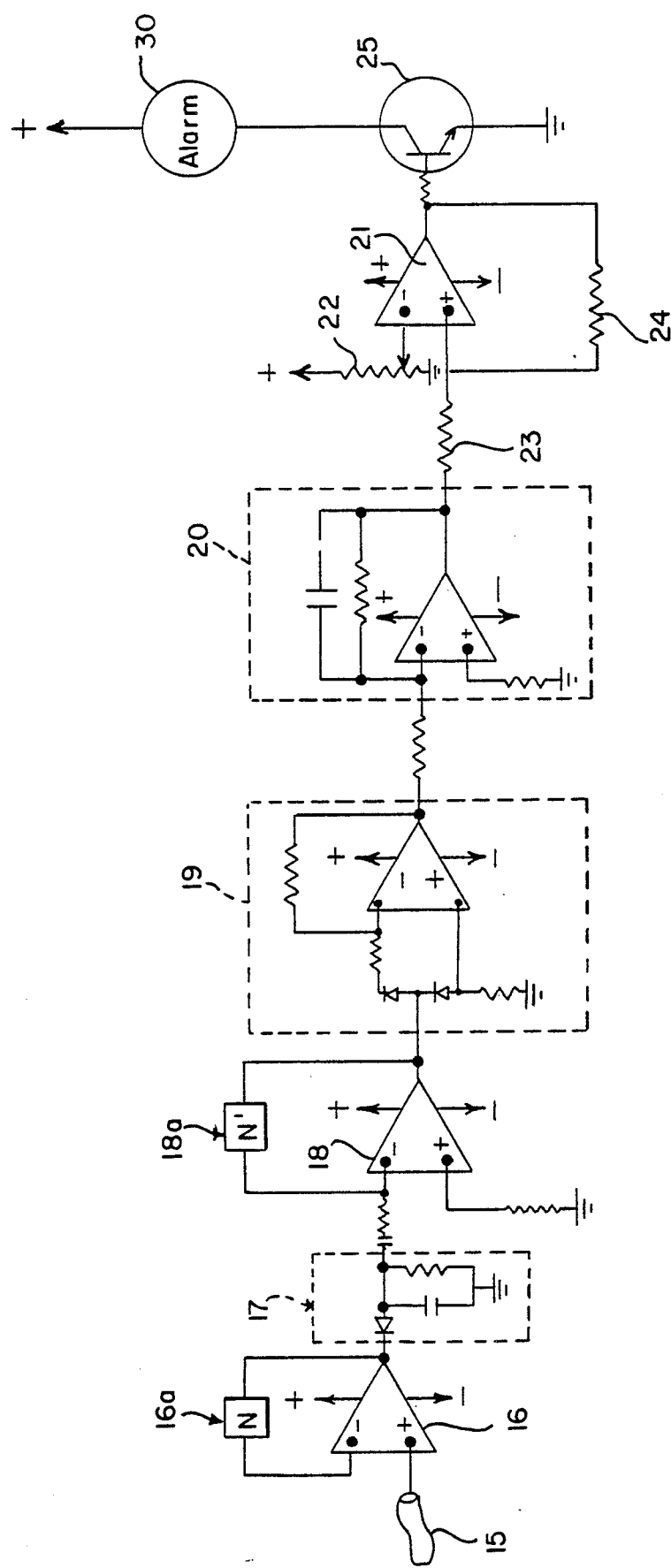
FIG. 2 is a partial schematic diagram of the elements of the electronic control system.

FIG. 2 is a detailed drawing showing the subsystems of the electronics 29. A shielded cable 15 conveys the electrical signal from the impedance bridge 27 to a first amplifier 16 which preferably includes a feedback network 16A. Said first amplifier 16 has a relatively narrow passband centered at the sonic operating frequency.

The amplified signal is demodulated by a peak detector diode and network 17 to derive the "clenching frequency", that is, the characteristic frequency of the upper and lower teeth coming together during bruxing as exemplified previously in the discussion relative to FIG. 1. For this example, the peak detector diode will recover a 1 Hz square wave that passes to the second amplifier 18 and feedback network 18A which has a passband to accommodate the "clenching frequency."

The signal from said second amplifier 18 then passes to a full-wave rectifier 19, thence to an electronic integrator 20. Said integrator 20 builds up to the trigger level of switch 21 when substantial bruxing occurs but discriminates against "transients" or stray signals.

Switch 21 has a trigger level and hysteresis determined by the values of a potentiometer 22, input resistance 23 and positive feedback resistance 24. Because of said hysteresis a threshold bruxing signal will result in switch 21 remaining closed for a finite period of time. The resultant signal then passes through n-p-n transistor 25 and activates alarm 14 for a sufficient period of time to alert the sleeping user that bruxing is occurring.

I claim:

1. An apparatus for the control and prevention of bruxing of bruxing comprising:
   a sound generating means adapted to be mounted on one of a subject's lower jaw or bony structure connected to the upper jaw,
   an adjustable electrical signal generator means for transmitting a signal to said sound generating means,
   an impedance measuring means located on line between said electrical signal generator means and said sound generating means,
   and electronic control means for detecting predetermined variations in signal voltage coming from said impedance measuring means, said variations in signal voltage resulting from variations in impedance which occur with the onset of bruxing, and
   an alarm means for alerting the subject when bruxing occurs, said alarm means being activated by said electronic control means when predetermined variations in impedance occur at the onset of bruxing.

2. The apparatus as recited in claim 1 wherein said electronic control means includes a first amplifier, a peak detector means, a second amplifier, a full wave rectifier, an electronic signal integrator and a switching means with a built-in hysteresis characteristic.

* * * * *